US00PP11160P

United States Patent [19]

Bak et al.

[11] Patent Number: Plant 11,160

[45] Date of Patent: Dec. 21, 1999

[54] GUZMANIA PLANT NAMED 'TWIST'

[75] Inventors: Elly Bak, Rijsenhout; Nicolaas D. Steur, Oude Niedorp, both of Netherlands

[73] Assignee: Corn. Bak B.V., Assendelft, Netherlands

[21] Appl. No.: 08/903,810

[22] Filed: Aug. 1, 1997

[51] Int. Cl.[6] ..... A01H 5/00

[52] U.S. Cl. ..... Plt./371

[58] Field of Search ..... Plt./88.8, 371

[56] References Cited

U.S. PATENT DOCUMENTS

P.P. 8,514 12/1993 Bak et al. ..... Plt./88.8

P.P. 9,467 3/1996 Kent ..... Plt./88.8

P.P. 10,369 4/1998 Bak et al. ..... Plt./88.8

*Primary Examiner*—Howard J. Locker

*Assistant Examiner*—Kent L. Bell

*Attorney, Agent, or Firm*—Foley & Lardner

[57] ABSTRACT

A new cultivar of Guzmania named 'Twist' characterized by a plant form that is funnel-form rosette; plant height of approximately 40 cm; linear-lanceolate leaves measuring 25–40 cm in length and 3–4 cm in width; leaf color upperside of R.H.S. 146A and underside of R.H.S. 146A; and primary bract color of R.H.S. 64A suffused with R.H.S. 156D, color of R.H.S. 156D.

2 Drawing Sheets

The present invention relates to a new and distinct cultivar of Guzmania that is an inter-specific hybrid, hereinafter referred to by the cultivar name 'Twist'.

BACKGROUND OF THE INVENTION

Guzmania are predominantly epiphytic with a few terrestrial species and are native to the tropics. For the most part species vary in diameter from 7 or 8 inches to 3 or 4 feed and have rosettes of glossy, smooth edged leaves.

Floral bracts of Guzmania frequently have brilliant colors and may last for many months. The range of colors for Guzmania is generally from yellow through orange but may also include flame red and red-purple. White or yellow, tubular, three petalled flowers may also appear on a stem or within the leaf rosette but are usually short lived.

Guzmania may be advantageously grown as pot plants for greenhouse or home use. Desirably the plants are shaded from direct sunlight and during the spring to autumn period the central vase-like part of the leaf rosette is desirably filled with water.

Guzmania is native to tropical America. Leaves of Guzmania are usually formed as basel rosettes which are stiff and entire and in several vertical ranks. Guzmania have terminal spikes or panicles which are often bracted with petals united in a tube about as long as the calyx. The ovary is superior and the seeds plumose.

Asexual propagation of Guzmania is frequently done through the use of tissue culture practices. Propagation can also be from off-shoots produced by the plant which may then be rooted. The resulting plantlets are detached from the mother plant and may be potted up in a suitable growing mixture.

Methods for cultivation and crossing of Guzmania are well known. For a detailed discussion, reference is made to the following publications, which are incorporated herein by reference. Benzing, David H., *The Biology of the Bromeliads*, Mad River Press, Inc., Eureka (1980); Zimmer, Karl, *Bromelien*, Verlag Paul Parey, Berlin (1986); and Rauh, Werner, *Bromelien*, Verlag Eugen Ulmer, Stuttgart (1981).

The new cultivar 'Twist' is a product of a planned breeding program and was originated by the inventors from a cross made during such a program in Assendelft, The Netherlands, in 1987. The male or pollen parent was a proprietary selection of *Guzmania wittmackii minor* identified by Code No. 8719802. The female or seed parent was a proprietary selection of *Guzmania lingulata minor* identified by Code No. 8719801.

The selection comprising the new variety was chosen from among progeny of the above cross following commencment of flowering in 1989 in Assendelft, The Netherlands. The selection was first asexually propagated through off-shoots by, or under the supervision of, the inventors in Assendelft, with subsequent asexual reproduction through tissue culture. Continuous asexual propagation has demonstrated that the combination of characteristics as herein disclosed for the new cultivar 'Twist', as observed in Assendelft, the Netherlands, are firmly fixed and are retained through successeive generations of asexual reproduction.

'Twist' has not been tested under all available environmental conditions. The phenotype may vary with variations in environmental conditions such as temperature, light intensity, frequency of fertilization, composition of fertilizer, acetylene treatment, day length and humidity without, however, any change in the genotype of the new cultivar.

The closest comparison cultivars are 'Limbo' U.S. Plant Pat. No. 8,514 and 'Salsa' U.S. Plant Pat. No. 10,369. In comparison to 'Limbo' and 'Salsa', the cultivar 'Twist' has a greater lilac part of the inflorescence and a brighter cream-white part. Overall, 'Twist' has a more compact growth habit and produces a lilac-white inflorescence.

BRIEF SUMMARY OF THE INVENTION

'Twist' is particularly characterized by the following characteristics:

1. Plant form that is a funnel-shaped rosette;

2. Plant height of approximately 40 cm;

3. Linear lanceolate leaves measuring 25–40 cm in length and 3–4 cm in width;

4. Leaf color upperside is R.H.S. 146A and underside of R.H.S. 146A;

5 Primary bract color is R.H.S. 64A suffused with R.H.S. 156D;

6. Tip of the primary bract is 64A; and

7. Top bract color is R.H.S. 156D.

BRIEF DESCRIPTION OF THE DRAWINGS

The accompanying color photographs show typical inflorescence and foliage characteristics of 'Twist', with the colors being as nearly true as possible with illustrations of this type.

Sheet 1 is a side view of a specimen of 'Twist' showing the primary and floral bracts.

Sheet 2 is a close-up of the floral bracts.

DETAILED BOTANICAL DESCRIPTION

The following traits have been repeatedly observed and in combination distinguish 'Twist' as a new and distinct cultivar. The following observations, measurements and descriptions were taken for 'Twist' plants grown under the following greenhouse conditions in Assendelft, The Netherlands. The minimum day and night temperature was 20 and 18° C., respectively. The ventilation temperature was 24° C. and the maximum light intensity was 18000 Lux. Fertilizer concentration was 0.5 to 1 EC comprising N:P:K in the ratio of 1:0.25 to 0.5:2 to 3. In addition, 3% of the total amount of fertilizer was $MgSO_4$.

Frequency of fertilization varied depending on time of year and ranged from once per week to once per month. Fertilization was more frequent during the spring and summer months. Following fertilization, the plants were rinsed with sufficient clean water to remove residual fertilizer from the leaves.

With regard to induction of flowering, acetylene gas is allowed to bubble through 100 L of cool water for 30 min at a pressure of 0.5 bar. Whole plants are then sprayed with the acetylene solution making certain that the cup (vase) is filled. Spraying is done in the morning because the plants need light after this treatment and the plants are not watered again for at least two days. The plants are treated again, following this same protocol, one week later. Plants should not be fertilized for two to three weeks following treatment with acetylene because it is likely the flowers will not form and the bracts will remain green.

I. Plant:

*Form.*—Funnel form rosette.

*Height.*—Approximately 40 cm high when flowering.

*Growth habit.*—Stemless.

*Diameter.*—Approximately 55 cm.

II. Foliage:

*Size of leaf.*—Length approximately 25–40 cm and width approximately 3–4 cm.

*Shape of leaf.*—Linear-lanceolate.

*Surface texture.*—Smooth.

*Margin.*—Entire.

*Apex.*—Acute.

*Color.*—Upperside R.H.S. 146A. Underside R.H.S. 146A.

III. Bracts:

*Length.*—Scape bracts range from approximately 23 cm at the bottom of plant to approximately 14 cm just below the primary bracts. Primary bracts range from approximately 13 cm to approximately 5 cm at the top of the plant.

*Width.*—Scape bracts are approximately 3.5 cm; and primary bracts are approximately 3.0 cm wide.

*Number.*—Scape bracts number approximately 10 and primary bracts number approximately 14.

*General shape.*—Lanceolate.

*Texture.*—Smooth.

*Margin.*—Entire.

*Color.*—Majority of primary bracts are R.H.S. 64A, suffused with R.H.S. 156D; tips of the primary bracts are R.H.S. 64A; and top primary bracts are approximately R.H.S. 156D (a few bracts possess a green coloration, approximately R.H.S. 146 A, towards their apices).

IV. Flowers:

*Borne (stalks).*—Erect.

*Shape of inflorescence.*—Compound.

*Size of inflorescence on stalk.*—Approximately 13 cm high.

*Diameter of inflorescence.*—Approximately 17 cm.

*Individual petals.*—(Mostly disposed within the floral bracts hidden under the primary bracts.). Length: Approximately 3.5 cm. Width: Approximately 0.4 cm. Quantity: Approximately 90 flowers spread over approximately 12 branches depending on the size of the plant. Color: White.

*Time of blooming.*—A fully grown plant can bloom the whole year beginning approximately 13 weeks after natural induction or through treatment with acetylene.

*Duration of blooms.*—Each flower blooms for 1 day and the total period of blooming following first bloom is about 6 weeks.

VI. Reproductive organs:

*Ovaries.*—Superior.

*Stamens.*—6.

*Seed characteristics.*—Sterile hybrid and therefore no fruit or seed is produced.

We claim:

1. A new an distinct cultivar of Guzmania plant named 'Twist', as illustrated and described.

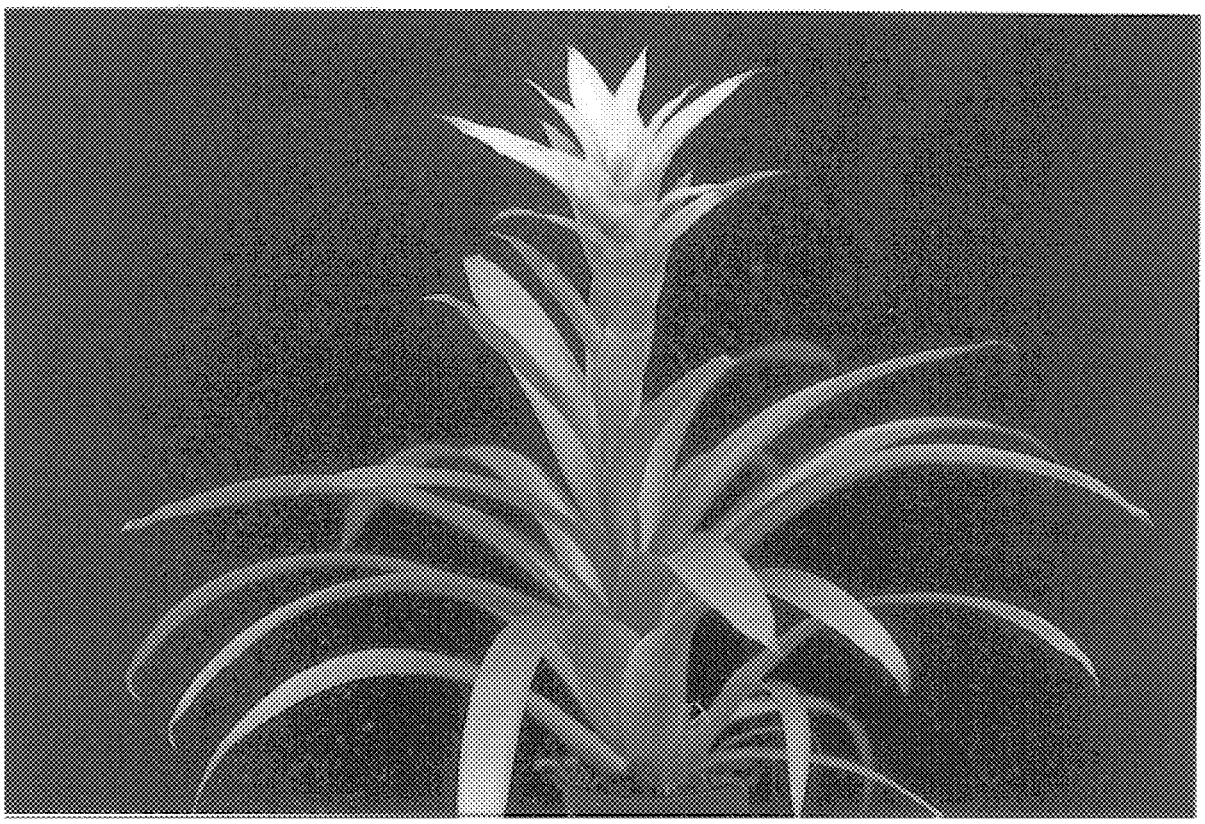

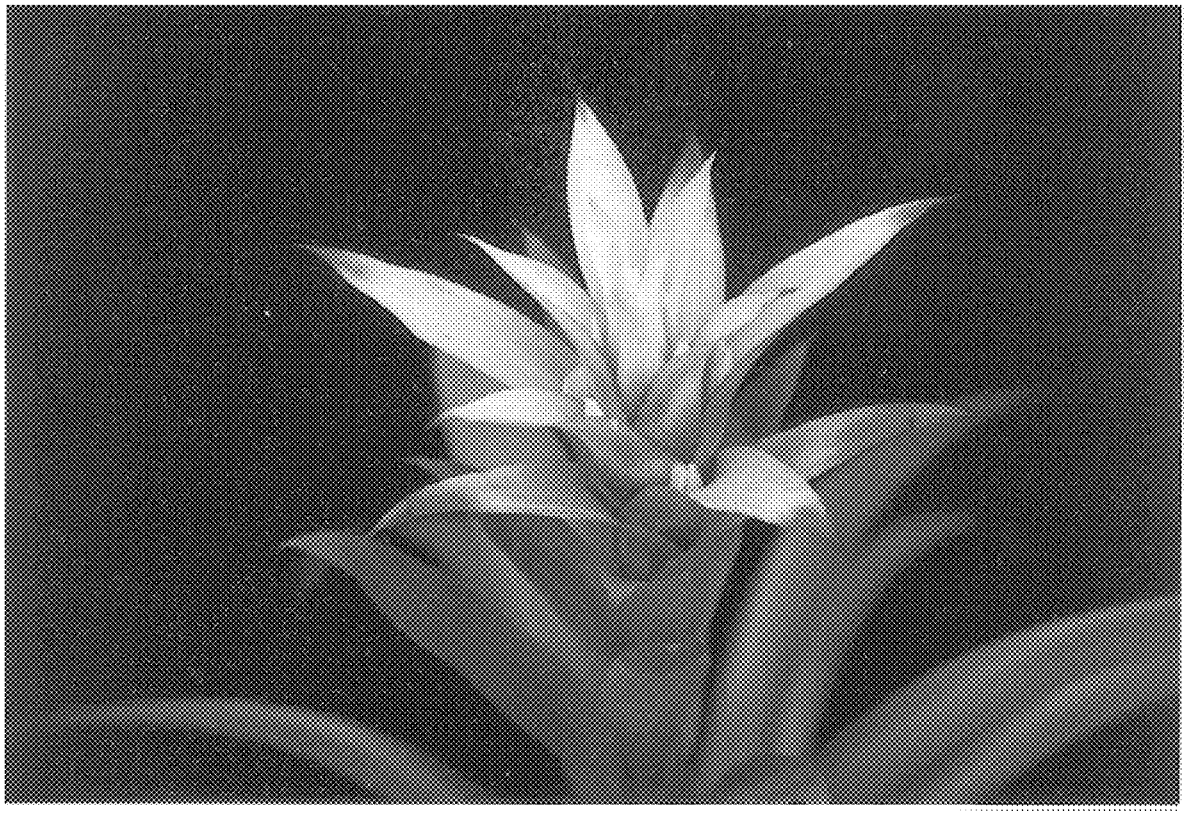

* * * * *